United States Patent
Zhao et al.

(10) Patent No.: US 9,522,866 B2
(45) Date of Patent: Dec. 20, 2016

(54) METHODS FOR PREPARING METHACROLEIN FROM T-BUTANOL

(71) Applicants: Shanghai HuaYi New Material Co., Ltd., Shanghai (CN); Shanghai HuaYi Acrylic Acid Co., Ltd., Shanghai (CN)

(72) Inventors: Xiaoqi Zhao, Shanghai (CN); Ge Luo, Shanghai (CN); Yong Chen, Shanghai (CN); Chunhua Qin, Shanghai (CN); Tonghao Wu, Shanghai (CN); Yan Zhuang, Shanghai (CN); Jianxue Ma, Shanghai (CN); Xiaodong Chu, Shanghai (CN); Jinhua Ji, Shanghai (CN)

(73) Assignees: Shanghai Huayi New Material Co., Ltd, Shanghai (CN); Shanghai HuaYi Acrylic Acid Co. Ltd., Shanghai (CN)

( * ) Notice: Subject to any disclaimer, the term of this patent is extended or adjusted under 35 U.S.C. 154(b) by 0 days.

(21) Appl. No.: 14/959,576

(22) Filed: Dec. 4, 2015

(65) Prior Publication Data

US 2016/0185698 A1    Jun. 30, 2016

(30) Foreign Application Priority Data

Dec. 31, 2014 (CN) .......................... 2014 1 0853472

(51) Int. Cl.
*C07C 45/37* (2006.01)
*B01J 23/888* (2006.01)

(52) U.S. Cl.
CPC ............ *C07C 45/37* (2013.01); *B01J 23/8885* (2013.01)

(58) Field of Classification Search
CPC ........ C07C 45/37; C07C 45/38; B01J 23/8885
USPC .......................................................... 568/471
See application file for complete search history.

(56) References Cited

U.S. PATENT DOCUMENTS

| | | | | |
|---|---|---|---|---|
| 5,144,090 A | * | 9/1992 | Honda | .................... B01J 23/002 568/476 |
| 6,399,818 B2 | * | 6/2002 | Tanimoto | ................ C07C 45/32 562/546 |
| 8,247,344 B2 | * | 8/2012 | Shin | ....................... B01J 23/002 502/312 |

\* cited by examiner

*Primary Examiner* — Sikarl Witherspoon
(74) *Attorney, Agent, or Firm* — Quarles & Brady, LLP

(57) ABSTRACT

A method for preparing methacrolein from t-butanol, specifically a method for preparing methacrolein by using t-butanol as a starting material, is disclosed, comprising passing the starting material through a fixed bed reactor filled with catalyst, wherein the fixed bed reactor is divided to n reaction zones from the inlet of the starting material to the outlet of the starting material and each zone is filled with catalysts of different catalytic activities; wherein the catalytic activity of the catalyst in the first reaction zone is higher than the catalytic activity of the catalyst in the second reaction zone, and the catalytic activity of the catalyst is gradually increased from the second reaction zone to the last reaction zone; and n is an integer between 3 to 10.

8 Claims, No Drawings

METHODS FOR PREPARING METHACROLEIN FROM T-BUTANOL

CROSS-REFERENCE TO RELATED APPLICATIONS

This Application claims priority to the Chinese Application Serial No. CN 201410853472.1, filed on Dec. 31, 2014, which is incorporated herein by reference for all purposes.

STATEMENT REGARDING FEDERALLY SPONSORED RESEARCH AND DEVELOPMENT

N/A

BACKGROUND OF THE INVENTION

Technical Field

The present invention relates to a method for preparing methacrolein by the reaction of t-butanol or a t-butanol-containing gas with molecular oxygen or a molecular oxygen-containing gas in a fixed bed reactor filled with catalysts.

Background

The process for the preparation of methacrolein from t-butanol or a t-butanol-containing gas comprises two chemical reactions, one is t-butanol being dehydrated to form isobutene, and the other is isobutene being oxidized to form methacrolein. Since such an oxidation reaction is a strong exothermic reaction, there is an area, i.e., hot spot, within the catalyst bed where the heat is intensively released. The temperature at the hot spot is very high, leading to an excessive oxidation reaction, accelerating thermal cracking of the catalyst, or even leading to temperature runaway phenomenon. Several solutions have been reported to solve the above problems. For example, it has disclosed a method for producing methacrolein and/or methacrylic acid by using t-butanol as a starting material, comprising supplying t-butanol to a fixed-bed multi-tubular reactor having a dehydration catalyst layer and an oxidation catalyst layer for dehydrating t-butanol to produce isobutene, and oxidizing isobutene to produce methacrolein and/or methacrylic acid. The dehydration catalyst layer comprises a catalyst containing alumina or alumina-silica and the filling length of this catalyst is from 3 to 20% of the filling length of the oxidation catalyst layer. This filling manner results in shortages, such as, extending the total length of the filler within the bed and, in turn, increasing the pressure drop during reaction, which may lead to increased temperature in the hot spot within the oxidation catalyst bed and decreased reaction selectivity.

The prior art has disclosed a method for producing methacrolein by using isobutene as a starting material, comprising a two-step catalytic oxidation during reaction by using two reactors in series. The first reactor is filled with an assistant catalyst having low activity and high selectivity and the second reactor is filled with a main catalyst having high activity and high selectivity. However, this filling manner increases the numbers and sizes of the reactors, resulting in increased investment of device and decreased economical efficiency of the project.

The prior art has further disclosed to fill the catalysts having different catalytic activities in upper zone and lower zone of a reaction tube such that the catalytic activities thereof can be gradually increased along the direction from the gas inlet to the gas outlet. However, since the temperature of the raw gas introduced into the catalyst layer in a gas-solid phase catalytic oxidation is generally lower than the reaction temperature, the raw gas needs to be pre-heated to obtain an effective catalytic efficiency. It is conventional to provide a pre-heating zone at the inlet of the raw gas. However, if the pre-heating zone is not provided or such a zone is relatively short, the raw gas, which has relative low temperature, rarely proceeds with the reaction when contacting with the catalyst having lower activity in the inlet. This is not economic because of the expensive catalyst being function as a medium of pre-heating zone. In addition, even if there is a pre-heating zone, the reaction temperature at the inlet of the bed will still be relative low if t-butanol is used as a starting material, as dehydration of t-butanol to isobutene is an endothermic reaction. Under this low temperature, the reaction efficiency will be very low if the catalyst having low activity is used to contact the starting material.

Therefore, there is still a need to develop a method to produce methacrolein by using t-butanol as a starting material, which method can effectively inhibit the formation of hot spot in the catalyst layer during the oxidation of methacrolein and, at the same time, can increase the utilization efficiency of the catalyst layer around the gas inlet.

SUMMARY OF THE INVENTION

Summary

The present invention intends to provide a cost effective method for producing methacrolein in high efficiency by using t-butanol as a starting material or a method for producing methacrolein by using isobutene as a starting material, which method can effectively inhibit the formation of hot spot in the catalyst layer during producing methacrolein by oxidation while increase the utilization efficiency of the catalyst layer around the gas inlet.

Therefore, in one aspect, the present invention relates to a method for producing methacrolein by using t-butanol as a starting material, comprising passing the starting material through a fixed bed reactor filled with catalysts, wherein the fixed bed reactor is divided into n reaction zones along the direction from the inlet of the starting material to the outlet, each zone is filled with a catalyst having different catalytic activity;

wherein the catalytic activity of the catalyst in the first reaction zone is higher than that in the second reaction zone, and the catalytic activity is gradually increased along the direction from the second reaction zone to the last reaction zone; and n is an integer between 3 to 10.

DETAILED DESCRIPTION OF THE INVENTION

Specific Mode for Carrying Out the Invention

The present invention relates to a method for producing methacrolein by using t-butanol as a starting material. The present invention also relates to a method for producing methacrolein by using isobutene as a starting material. The methods of the present invention comprise performing a catalytic reaction in a fixed bed reactor.

The catalysts suitable for use in the method of the present invention are not specifically limited and can be any conventional catalysts known in the art, as long as the catalysts have different catalytic activities. In one embodiment of the present invention, the catalysts are selected from:

(i) a compound having formula (I):

$$x(Mo_aW_bFe_cBi_dCo_eNi_fA_gO_h)/yZ \quad (I)$$

wherein Mo, W, Fe, Bi, Co, Ni and O refer to molybdenum element, tungsten element, ferrum element, bismuth element, cobalt element, nickel element and oxygen element, respectively;

A is at least one element selected from the group consisting of potassium, sodium, rubidium and cesium;

Z is a carrier function as a dilution heat conduction agent, which is selected from the group consisting of silicon carbide, titania, or silica;

a, b, c, d, e, f, g and h each refers to the atom ratio of each element; when a=10~12, b=0~2 and a+b=12, others are 0.3≤c≤5, 0.3≤d≤3, 2≤e≤8, 0.1≤f≤3.5, 0.05≤g≤2.5, preferably 0.5≤c≤3, 0.5≤d≤2.5, 3≤e≤7, 0.3≤f≤2.5, 0.1≤g≤2; h is the atom ratio of oxygen required for satisfying the valance of each above-mentioned component;

x and y refer to the weights of the composite oxide catalyst and the dilution heat conduction agent Z, respectively; y/x=5~80% by weight, preferably 15~60% by weight; and (ii) a compound having formula (II):

$$m(Mo_aW_bFe_cBi_dCo_eE_iO_h)/nM \quad (II)$$

wherein Mo, W, Fe, Bi, Co and O refer to molybdenum element, tungsten element, ferrum element, bismuth element, cobalt element and oxygen element, respectively;

E is at least one element selected from the group consisting of potassium, sodium, rubidium, cesium, barium, magnesium and calcium;

M is a carrier function as a dilution heat conduction agent added during molding the catalyst, and is at least one of silicon carbide, titania, silica, zirconia or alumina;

a, b, c, d, e, i and h each refers to the atom ratio of each element; when a=10~12, b=0~2 and a+b=12, others are 0.3≤c≤5, 0.3≤d≤3, 2≤e≤8, and 0.01≤i≤2.0, preferably 0.5≤c≤3, 0.5≤d≤2.5, 3≤e≤7 and 0.1≤i≤1.5;

h is the atom ratio of oxygen required for satisfying the valance of each above-mentioned component;

m and n refer to the weights of the composite oxide catalyst and the dilution heat conduction agent M, respectively; n/m=5~80% by weight, preferably 20~60% by weight.

Generally, the compound of formula (II) has a lower catalyst activity than that of the compound of formula (I).

As used herein, the term "catalytic activity" refers to the ability of a catalyst in converting t-butanol or isobutene into its corresponding methacrolein. The catalyst having a relatively higher (lower) ability to convert the t-butanol or isobutene is called as a catalyst having higher (or lower) activity.

In one embodiment of the present invention, the catalyst used in the first reaction zone has a composition that is shown in the above formula (I) or (II), preferably shown in formula (II), while its catalytic activity is selected as required according to the type and/or amount of the element A and/or E, y/x ratio, n/m ratio or the calcining temperature of the catalyst.

Methods for selecting the catalytic activity by changing the type and/or amount of the element A and/or E, y/x ratio, n/m ratio of formula (I) or (II) or the calcining temperature of the catalyst are well known in the art. The skilled artisan can readily obtain the desired catalytic activity of a catalyst via conventional means.

The catalysts as shown in formulae (I) and (II) of the present invention can be prepared by any methods conventionally used for preparation of such kind of catalyst. The main difference between these two catalysts is the formula (I) comprising Ni element while the formula (II) does not. In case element A in formula (I) being the same one element as element E in formula (II), the amount of A in formula (I) is greater than the amount of E in formula (II).

In one embodiment of the present invention, each reaction tube of the shell-tube fixed bed reactor is divided into at least three reaction zones, which are first, second, third, . . . , reaction zones arranged along the reaction tube from the gas inlet to the gas outlet. The catalysts having different activities are filled in these reaction zones in which the catalyst having the lowest activity is filled in the second reaction zone and the catalyst having relatively high activity is filled in the reaction zone, i.e., the first reaction zone, adjacent to the gas inlet.

In one embodiment of the present invention, the following catalyst is used in each reaction zone:

Catalyst (A): 80 $(Mo_{10.0}W_{2.0}Fe_{2.1}Bi_{1.4}Co_{5.3}Ni_{0.5}Cs_{0.15})$/20SiC;

Catalyst (B): 90 $(Mo_{10.5}W_{1.5}Fe_{2.5}Bi_{1.3}Co_{6.2}Cs_{0.04})$/10SiO$_2$;

Catalyst (C): 80 $(Mo_{10.5}W_{1.5}Fe_{2.5}Bi_{1.3}Co_{6.2}Cs_{0.04})$/20SiC;

Catalyst (D): 85 $(Mo_{10.0}W_{2.0}Fe_{2.1}Bi_{1.4}Co_{5.3}Ni_{0.5}Cs_{0.15})$/15SiC;

Catalyst (E): 85 $(Mo_{10.5}W_{1.5}Fe_{2.5}Bi_{1.3}Co_{6.2}Cs_{0.04})$/15ZrO$_2$.

The catalytic activities of the above catalysts are as follows: catalyst (B)> catalyst (E)> catalyst (C)> catalyst (D)> catalyst (A).

In one embodiment of the present invention, the catalytic bed is divided into three reaction zones (or catalyst layers). The filling lengths of the first reaction zone ($L_1$) and the second reaction zone ($L_2$) as well as the total length of the three reaction zones (L) meet the following equations:

When the catalytic activity in the first reaction zone is higher than those in the second and third reaction zones, $$0 < \frac{L_1}{L} \le 0.3,$$

$$0 < \frac{L_2}{L} \le 0.8,$$

while $$0.3 \le \frac{L_1}{L} + \frac{L_2}{L} < 1,$$

preferably $$0 < \frac{L_1}{L} \le 0.2,$$

$$0 < \frac{L_2}{L} \le 0.6,$$

while $$0.4 \le \frac{L_1}{L} + \frac{L_2}{L} < 1;$$

when the catalytic activity in the first reaction zone is higher than that in the second reaction zone while is equal to that in the third reaction zone, $$0 < \frac{L_1}{L} \le 0.4,$$

-continued $$0 < \frac{L_2}{L} \leq 0.7,$$

while $$0.3 \leq \frac{L_1}{L} + \frac{L_2}{L} < 1,$$

preferably $$0 < \frac{L_1}{L} \leq 0.3,$$

$$0 < \frac{L_2}{L} \leq 0.5,$$

while $$0.4 \leq \frac{L_1}{L} + \frac{L_2}{L} < 1;$$

when the catalytic activity in the first reaction zone is higher than that in the second reaction zone and is lower than that in the third reaction zone, $$0 < \frac{L_1}{L} \leq 0.5,$$

$$0 < \frac{L_2}{L} \leq 0.6,$$

while $$0.3 \leq \frac{L_1}{L} + \frac{L_2}{L} < 1,$$

preferably $$0 < \frac{L_1}{L} \leq 0.4,$$

$$0 < \frac{L_2}{L} \leq 0.4,$$

while $$0.4 \leq \frac{L_1}{L} + \frac{L_2}{L} < 1;$$

the length ($L_3$) of the third reaction zone and the total length (L) of the three reaction zone satisfy the following equation:

$$\frac{L_3}{L} = 1 - \left(\frac{L_1}{L} + \frac{L_2}{L}\right).$$

The processes of the present invention can being about the following benefits:

(1) the starting material t-butanol can be quickly dehydrated to form isobutene while a portion of the formed isobutene is oxidized into methacrolein, thereby breaking the balance between the dehydration of t-butanol and hydration of isobutene, facilitating the reaction towards the formation of isobutene; and (2) use of the catalyst having relatively low activity in the second reaction zone can effectively reduce the temperature of the hot spot, resulting in a stable oxidation reaction and prolonging the lifetime of the catalyst.

Therefore, the present invention provides a method for producing methacrolein by dehydrating t-butanol and oxidizing, which comprises passing t-butanol or a t-butanol-containing gas together with molecular oxygen or a molecular oxygen-containing gas into a fixed bed reactor filled with catalysts. The method is characterized in that the catalytic activity of the catalyst filled in and around the gas inlet of the fixed bed reactor is higher than that of the catalyst filled in the adjacent zone or the second zone, such a catalyst is for dehydrating t-butanol and for catalyzing the oxidization reaction; upon passing through such a reaction zone or the first zone, the reaction gas passes through such a catalyst bed that the catalytic activities thereof are gradually increased along the direction from the gas inlet to the gas outlet; and the catalytic bed of the reactor is divided into at least three reaction zones along the machine direction, including the zone at the inlet for dehydrating t-butanol and catalyzing the oxidization reaction.

The method of the present invention can effectively solve the problem of the temperature being too low in the catalyst bed around the gas inlet due to low activity of the catalyst per se and endotherm caused by dehydration, can increase the utilization efficiency of the catalyst in the second zone, and can effectively inhibit accumulation of heat due to exotherm by oxidation in the second zone, reducing the irreversible damage on the catalyst and prolong its working life.

According to the present invention, the gas phase oxidation of the gas containing t-butanol is performed by contacting a gaseous mixture with the catalysts under 300-380° C., 0.2-1.2MPa, and a space velocity of 800~3200 $h^{-1}$. The gaseous mixture contains 2-12% by mol of t-butanol, molecular oxygen in an amount 2-6 times of the amount of t-butanol, and balance amount of inert gas, such as $N_2$, $CO_2$ and water vapor.

According to the present invention, the temperature difference between the hot spot within the catalyst layer and the reaction temperature can be reduced, in turn, the thermal deterioration of the catalyst can be effectively controlled, the catalyst can be used in stable for a long term, and the selectivity of the target product, methacrolein, can be improved. In addition, the length of the pre-heating zone in the bed can be reduced, thereby allowing the whole bed to have a low pressure and reducing the size of the reactor and investment cost of device.

The conversion rate of the starting material and the selectivity of methacrolein or methacrylic acid during reaction are calculated according to the following equations:

Conversion rate of t-butanol or isobutene=(mole of the reacted t-butanol or isobutene)/(mole of the added t-butanol or isobutene)×100%;

Selectivity of methacrolein=(mole of the produced methacrolein)/(mole of the reacted t-butanol or isobutene)×100%;

Selectivity of methacrylic acid=(mole of the produced methacrylic acid)/(mole of the reacted t-butanol or isobutene)×100%

The invention will be illustrated by the following specific Examples. The scope of the invention, however, is not limited by these Examples.

Example 1

(1) Preparation of Catalyst

Under stirring, 8000 g ammonium molybdate and 2573 g ammonium tungstate were dissolved in 18200 ml water at 70° C. to produce colorless and clear solution A; and 6991 g cobalt nitrate, 3844 g ferric nitrate, 659 g nickel nitrate, 3077 g bismuth nitrate and 133 g cesium nitrate were disclosed in 4500 ml water at 50° C. to produce solution B.

Solution B was slowly added to solution A to obtain a khaki slurry. The slurry was stirred at 70° C. for aging for 2 hours, transferred to a tray and drying in an oven at 120° C. for 12 hours. The dried substance was removed from the oven and ground and then pre-calcined in a 200° C. furnace to produce catalyst precursor powder (i).

80 parts by mass of the catalyst precursor powder (i), 20 parts by mass of SiC powder, 3 parts by mass of graphite, 3 parts by mass of a granulating auxiliary (silica sol) and a suitable amount of water were homogenously mixed and subjected to granulation to form particles in a form of Raschig ring with an external diameter of 5 mm, an inner diameter of 2 mm and a height of 5 mm. The granulated particles were calcined in air at 530° C. for 10 hours to produce a catalyst with a composition of 80 $(Mo_{10.0}W_{2.0}Fe_{2.1}Bi_{1.4}Co_{5.3}Ni_{0.5}Cs_{0.15})/20SiC$ (called as catalyst (A)).

According to the same method for preparing catalyst (A), under stirring, 18000 g ammonium molybdate and 4,135 g ammonium tungstate were dissolved in 40,800 ml water at 70° C. to produce colorless and clear solution A; and 17,525 g cobalt nitrate, 9,807 g ferric nitrate, 6,123 g bismuth nitrate and 76 g cesium nitrate were disclosed in 11,000 ml water at 50° C. to produce solution B. Solution B was slowly added to solution A to obtain a khaki slurry. The slurry was stirred at 70° C. for aging for 2 hours, transferred to a tray and placed in an oven for drying at 120° C. for 12 hours. The dried substance was removed from the oven and ground and then pre-calcined in a 200° C. furnace to produce catalyst precursor powder (ii).

90 parts by mass of the catalyst precursor powder (ii), 10 parts by mass of $SiO_2$ powder, 3 parts by mass of graphite, 3 parts by mass of a granulating auxiliary (silicasol) and a suitable amount of water were homogenously mixed and subjected to granulation to form particles in a form of Raschig ring with an external diameter of 5 mm, an inner diameter of 2 mm and a height of 5 mm. The granulated particles were calcined in air at 520° C. for 10 hours to produce a catalyst with a composition of 90 $(Mo_{10.5}W_{1.5}Fe_{2.5}Bi_{1.3}Co_{6.2}Cs_{0.04})/10SiO_2$ (called as catalyst (B)).

80 parts by mass of the catalyst precursor powder (ii), 20 parts by mass of SiC powder, 3 parts by mass of graphite, 3 parts by mass of a granulating auxiliary (silicasol) and a suitable amount of water were homogenously mixed and subjected to granulation to form particles in a form of Raschig ring with an external diameter of 5 mm, an inner diameter of 2 mm and a height of 5 mm. The granulated particles were calcined in air at 520° C. for 10 hours to produce a catalyst with a composition of 80 $(Mo_{10.5}W_{1.5}Fe_{2.5}Bi_{1.3}Co_{6.2}Cs_{0.04})/20SiC$ (called as catalyst (C)).

(2) Evaluation of the Performance of the Catalyst

The starting material t-butanol (85% by mass) and air, nitrogen were metered by a constant-flux pump and a mass flowmeter, respectively, mixed, pre-heated, and introduced into a reactor. The reactor had a length of 3,500 mm and an inner diameter of 27 mm, with a thermowell having an external diameter of 8 mm equipped in the middle of the reactor for measuring the temperature within the catalyst layer. A pre-heated layer of alumina spheres (5 mm diameter) having a length of 200 mm, catalyst (B) having a length of 200 mm, catalyst (A) having a length of 1,000 mm, and catalyst (C) having a length of 1,800 mm were successively filled along the direction from the gas inlet to the gas outlet. Oxidization was performed at t-butanol:oxygen:nitrogen:water=1:2:12:0.7 (molar ratio) and a space velocity of mixed gas of 1,000 $h^{-1}$. Results were obtained after 1,000 hours of reaction and were shown in Table 1.

Comparative Example 1

The reaction conditions were identical to Example 1, except that the whole catalyst bed was filled with catalyst (A) having a length of 3,000 mm without the use of catalyst (B) and catalyst (C). The reaction results were shown in Table 1.

Comparative Example 2

The reaction conditions were identical to Example 1, except that the whole catalyst bed was filled with catalyst (B) having a length of 3,000 mm without the use of catalyst (A) and catalyst (C). The reaction results were shown in Table 1.

Comparative Example 3

The reaction conditions were identical to Example 1, except that the whole catalyst bed was filled with catalyst (C) having a length of 3,000 mm without the use of catalyst (A) and catalyst (B). The reaction results were shown in Table 1.

Example 2

(1) Preparation of Catalyst

Catalyst powder (i) was obtained according to the same process as that of Example 1. 85 parts by mass of the catalyst precursor powder (i), 15 parts by mass of SiC powder, 3 parts by mass of graphite, 3 parts by mass of a granulating auxiliary (silica sol) and a suitable amount of water were homogenously mixed and subjected to granulation to form particles in a form of Raschig ring with an external diameter of 5 mm, an inner diameter of 2 mm and a height of 5 mm. The granulated particles were calcined in air at 530° C. for 10 hours to produce a catalyst with a composition of 85 $(Mo_{10.0}W_{2.0}Fe_{2.1}Bi_{1.4}Co_{5.3}Ni_{0.5}Cs_{0.15})/15SiC$ (called as catalyst (D)).

Catalyst powder (ii) was obtained according to the same process as that of Example 1. 85 parts by mass of the catalyst precursor powder (ii), 15 parts by mass of $ZrO_2$ powder, 3 parts by mass of graphite, 3 parts by mass of a granulating auxiliary (silicasol) and a suitable amount of water were homogenously mixed and subjected to granulation to form particles in a form of Raschig ring with an external diameter of 5 mm, an inner diameter of 2 mm and a height of 5 mm. The granulated particles were calcined in air at 520° C. for 10 hours to produce a catalyst with a composition of 85 $(Mo_{10.5}W_{1.5}Fe_{2.5}Bi_{1.3}Co_{6.2}Cs_{0.04})/15ZrO_2$ (called as catalyst (E)).

(2) Oxidation

Oxidation was performed in the same manner as that in Example 1, except that the catalysts and their heights in the catalyst bed were changed to be pre-heated layer of alumina spheres (5 mm diameter) in a length of 200 mm, catalyst (E) in a length of 250 mm, catalyst (D) in a length of 800 mm, and catalyst (C) in a length of 1,950 mm along the direction from the gas inlet to the gas outlet. The reaction results were shown in Table 1.

Comparative Example 4

The reaction conditions were identical to Example 2, except that the whole catalyst bed was filled with catalyst (D) having a length of 3000 mm without the use of catalyst (E) and catalyst (C). The reaction results were shown in Table 1.

Comparative Example 5

The reaction conditions were identical to Example 2, except that the whole catalyst bed was filled with catalyst (E) having a length of 3000 mm without the use of catalyst (D) and catalyst (C). The reaction results were shown in Table 1.

Examples 3-5

The reaction conditions were identical to Example 1, except that the catalysts and their lengths were changed. And the results after 1000 h of reaction were shown in Table 1.

Comparative Examples 6-10

The reaction conditions were identical to Example 1, except that the catalysts and their lengths were changed. And the results after 500 h or 1,000 h of reaction were shown in Table 1.

According to the results shown in Table 1, the catalytic activity of an individual catalyst used in the above Examples and Comparative Examples are in an order of catalyst (B)>catalyst (E)>catalyst (C)>catalyst (D)>catalyst (A).

In Examples 1-5, the catalysts were filled according to the method of the present invention. Thus, the reaction temperature of the catalyst layer and the temperature of the hot spot can be effectively reduced, and a relatively high selectivity for methacrolein and methacrylic acid can be obtained. On the contrary, in Comparative Examples 6-10, the catalytic activity was monotonically increased from the gas inlet to the gas outlet, resulting in poor reaction performance of the catalyst.

What is claimed is:

1. A method for producing methacrolein by using t-butanol as a starting material, comprising passing the starting material through a fixed bed reactor filled with catalysts, wherein the fixed bed reactor is divided to n reaction zones along the direction from the inlet to the outlet of the starting material, each zone is filled with a catalyst having different catalytic activity;

wherein the catalytic activity of the catalyst in the first reaction zone is higher than that of the catalyst in the second reaction zone; and the catalytic activities of the catalysts are gradually increased from the second reaction zone to the last reaction zone; and n is an integer between 3 to 10.

TABLE 1

Filling of the Catalyst Bed and the Reaction Results

| | Catalysts filled along the direction from the gas inlet to the gas outlet and their lengths (mm) | Reaction Time (h) | Reaction Temperature (° C.) | Temperature of Hot Spot (° C.) | Conversion Rate (%) | MAL Selectivity (%) | MAA Selectivity (%) |
|---|---|---|---|---|---|---|---|
| Example 1 | catalyst (B)/(A)/(C): 200/1000/1800 | 1000 | 355 | 412 | 99.1 | 84.2 | 2.1 |
| Com. Ex. 1 | catalyst (A)/3000 | 500 | 370 | 397 | 72.3 | 91.2 | 3.0 |
| Com. Ex. 2 | catalyst (B)/3000 | 500 | 340 | 420 | 99.2 | 85.6 | 2.2 |
| Com. Ex. 3 | catalyst (C)/3000 | 500 | 350 | 413 | 99.1 | 86.5 | 2.5 |
| Example 2 | catalyst (E)/(D)/(C): 250/800/1950 | 1000 | 355 | 405 | 99.1 | 85.8 | 2.6 |
| Com. Ex. 4 | catalyst (D)/3000 | 500 | 370 | 402 | 80.5 | 89.6 | 2.9 |
| Com. Ex. 5 | catalyst (E)/3000 | 500 | 345 | 415 | 98.8 | 85.7 | 1.8 |
| Example 3 | catalyst (C)/(A)/(C): 400/1000/1600 | 1000 | 360 | 408 | 99.0 | 84.3 | 2.4 |
| Example 4 | catalyst (D)/(A)/(E): 500/1200/1300 | 1000 | 358 | 415 | 99.0 | 83.0 | 1.8 |
| Com. Ex. 6 | (A)/(C): 1000/2000 | 1000 | 363 | 422 | 98.9 | 83.5 | 1.9 |
| Com. Ex. 7 | (D)/(C): 1000/2000 | 1000 | 358 | 420 | 99.1 | 82.9 | 2.5 |
| Com. Ex. 8 | (A)/(D): 1000/2000 | 500 | 370 | 410 | 98.5 | 83.3 | 2.8 |
| Com. Ex. 9 | catalyst (A)/(C)/(B): 1000/1800/200 | 1000 | 360 | 418 | 99.0 | 83.2 | 2.2 |
| Example 5 | catalyst (E)/(D)/(B): 250/800/1950 | 1000 | 352 | 407 | 99.0 | 84.2 | 2.0 |
| Com. Ex. 10 | (D)/(B): 1000/2000 | 500 | 356 | 405 | 98.8 | 83.6 | 2.1 |

2. The method according to claim 1, wherein the catalyst is selected from:
(i) a compound having formula (I): $x(Mo_aW_bFe_cBi_dCo_eNi_fA_gO_h)/yZ$ (I)

wherein Mo, W, Fe, Bi, Co, Ni and O refer to molybdenum element, tungsten element, ferrum element, bismuth element, cobalt element, nickel element and oxygen element, respectively;

A is at least one element selected from the group consisting of potassium, sodium, rubidium and cesium;

Z is a carrier function as a dilution heat conduction agent and is silicon carbide, titania, or silica;

a, b, c, d, e, f g and h each refers to the atom ratio of each element; when a=10~12, b=0~2 and a+b=12, 0.3≤c≤5, 0.3≤d≤3; 2≤e≤8, 0.1≤f≤3.5, 0.05≤g≤2.5; h is the atom ratio of oxygen required for satisfying the valance of each above-mentioned component;

x and y refer to the mass of the composite oxide catalyst and the mass of the dilution heat conduction agent Z, respectively; y/x=5~80% by mass; and (ii) a compound having formula (II):

$m(Mo_aW_bFe_cBi_dCo_eE_iO_h)/nM$ (II)

wherein Mo, W, Fe, Bi, Co and O refer to molybdenum element, tungsten element, ferrum element, bismuth element, cobalt element and oxygen element, respectively;

E is at least one element selected from the group consisting of potassium, sodium, rubidium, cesium, barium, magnesium and calcium;

M is a carrier function as a heat conduction agent added during molding of the catalyst and is at least one of silicon carbide, titania, silica, zirconia or alumina;

a, b, c, d, e, i and h each refers to the atom ratio of each element; when a=10~12, b=0~2 and a+b=12, 0.3≤c≤5, 0.3≤d≤3, 2≤e≤8, and 0.01≤i≤2.0;

h is the atom ratio of oxygen required for satisfying the valance of each above-mentioned component;

m and n refer to the mass of the composite oxide catalyst and the mass of the dilution heat conduction agent M, respectively; n/m=5~80% by mass.

3. The method according to claim 2, wherein the compound of formula (II) has a lower catalytic activity than that of the compound of formula (I).

4. The method according to claim 1, wherein the following catalysts are used:

Catalyst (A): 80 $(Mo_{10.0}W_{2.0}Fe_{2.1}Bi_{1.4}Co_{5.3}Ni_{0.5}Cs_{0.15})$/20SiC;

Catalyst (B): 90 $(Mo_{10.5}W_{1.5}Fe_{2.5}Bi_{1.3}Co_{6.2}Cs_{0.04})$/10SiO_2;

Catalyst (C): 80 $(Mo_{10.5}W_{1.5}Fe_{2.5}Bi_{1.3}Co_{6.2}Cs_{0.04})$/20SiC;

Catalyst (D): 85 $(Mo_{10.0}W_{2.0}Fe_{2.1}Bi_{1.4}Co_{5.3}Ni_{0.5}Cs_{0.15})$/15SiC;

Catalyst (E): 85 $(Mo_{10.5}W_{1.5}Fe_{2.5}Bi_{1.3}Co_{6.2}Cs_{0.04})$/15ZrO_2; and the catalytic activities of these catalysts are in an order of catalyst (B)>catalyst (E)>catalyst (C)>catalyst (D)>catalyst (A).

5. The method according to claim 1, wherein the fixed bed reactor is divided into three reaction zones, the filling lengths of the first reaction zone ($L_1$) and the second reaction zone ($L_2$) as well as the total length of the reaction zone (L) meet the following equation:

when the catalytic activity in the first reaction zone is higher than those in the second and the third reaction zone, $$0 < \frac{L_1}{L} \leq 0.3,$$

$$0 < \frac{L_2}{L} \leq 0.8,$$

while $$0.3 \leq \frac{L_1}{L} + \frac{L_2}{L} < 1;$$

when the catalytic activity in the first reaction zone is higher than that in the second reaction zone and is equal to that in the third reaction zone, $$0 < \frac{L_1}{L} \leq 0.4, \, 0 < \frac{L_2}{L} \leq 0.7, \text{ while } 0.3 \leq \frac{L_1}{L} + \frac{L_2}{L} < 1;$$

when the catalytic activity in the first reaction zone is higher than that in the second reaction zone and is lower than that in the third reaction zone, $$0 < \frac{L_1}{L} \leq 0.5, \, 0 < \frac{L_2}{L} \leq 0.6,$$

and at the same time $0.3 \leq \frac{L_1}{L} + \frac{L_2}{L} < 1;$ and the length of the third reaction zone ($L_3$) and the total length (L) of the reaction zone satisfies the following equation:

$$\frac{L_3}{L} = 1 - \left(\frac{L_1}{L} + \frac{L_2}{L}\right).$$

6. The method according to claim 2, wherein the fixed bed reactor is divided into three reaction zones, the filling lengths of the first reaction zone ($L_1$) and the second reaction zone ($L_2$) as well as the total length of the reaction zone (L) meet the following equation:

when the catalytic activity in the first reaction zone is higher than those in the second and the third reaction zone, $$0 < \frac{L_1}{L} \leq 0.3, \, 0 < \frac{L_2}{L} \leq 0.8, \text{ while } 0.3 \leq \frac{L_1}{L} + \frac{L_2}{L} < 1;$$

when the catalytic activity in the first reaction zone is higher than that in the second reaction zone and is equal to that in the third reaction zone, $$0 < \frac{L_1}{L} \leq 0.4, \, 0 < \frac{L_2}{L} \leq 0.7, \text{ while } 0.3 \leq \frac{L_1}{L} + \frac{L_2}{L} < 1;$$

when the catalytic activity in the first reaction zone is higher than that in the second reaction zone and is lower than that in the third reaction zone, $$0 < \frac{L_1}{L} \leq 0.5, \; 0 < \frac{L_2}{L} \leq 0.6,$$

and at the same time $0.3 \leq \frac{L_1}{L} + \frac{L_2}{L} < 1;$ and the length of the third reaction zone ($L_3$) and the total length (L) of the reaction zone satisfies the following equation:

$$\frac{L_3}{L} = 1 - \left(\frac{L_1}{L} + \frac{L_2}{L}\right).$$

7. The method according to claim 3, wherein the fixed bed reactor is divided into three reaction zones, the filling lengths of the first reaction zone ($L_1$) and the second reaction zone ($L_2$) as well as the total length of the reaction zone (L) meet the following equation:

when the catalytic activity in the first reaction zone is higher than those in the second and the third reaction zone, $$0 < \frac{L_1}{L} \leq 0.3, \; 0 < \frac{L_2}{L} \leq 0.8, \text{ while } 0.3 \leq \frac{L_1}{L} + \frac{L_2}{L} < 1;$$

when the catalytic activity in the first reaction zone is higher than that in the second reaction zone and is equal to that in the third reaction zone, $$0 < \frac{L_1}{L} \leq 0.4, \; 0 < \frac{L_2}{L} \leq 0.7, \text{ while } 0.3 \leq \frac{L_1}{L} + \frac{L_2}{L} < 1;$$

when the catalytic activity in the first reaction zone is higher than that in the second reaction zone and is lower than that in the third reaction zone, $$0 < \frac{L_1}{L} \leq 0.5, \; 0 < \frac{L_2}{L} \leq 0.6,$$

and at the same time $0.3 \leq \frac{L_1}{L} + \frac{L_2}{L} < 1;$ and the length of the third reaction zone ($L_3$) and the total length (L) of the reaction zone satisfies the following equation:

$$\frac{L_3}{L} = 1 - \left(\frac{L_1}{L} + \frac{L_2}{L}\right).$$

8. The method according to claim 4, wherein the fixed bed reactor is divided into three reaction zones, the filling lengths of the first reaction zone ($L_1$) and the second reaction zone ($L_2$) as well as the total length of the reaction zone (L) meet the following equation:

when the catalytic activity in the first reaction zone is higher than those in the second and the third reaction zone, $$0 < \frac{L_1}{L} \leq 0.3, \; 0 < \frac{L_2}{L} \leq 0.8, \text{ while } 0.3 \leq \frac{L_1}{L} + \frac{L_2}{L} < 1;$$

when the catalytic activity in the first reaction zone is higher than that in the second reaction zone and is equal to that in the third reaction zone, $$0 < \frac{L_1}{L} \leq 0.4, \; 0 < \frac{L_2}{L} \leq 0.7, \text{ while } 0.3 \leq \frac{L_1}{L} + \frac{L_2}{L} < 1;$$

when the catalytic activity in the first reaction zone is higher than that in the second reaction zone and is lower than that in the third reaction zone, $$0 < \frac{L_1}{L} \leq 0.5, \; 0 < \frac{L_2}{L} \leq 0.6,$$

and at the same time $0.3 \leq \frac{L_1}{L} + \frac{L_2}{L} < 1;$ and the length of the third reaction zone ($L_3$) and the total length (L) of the reaction zone satisfies the following equation:

$$\frac{L_3}{L} = 1 - \left(\frac{L_1}{L} + \frac{L_2}{L}\right).$$

* * * * *